United States Patent [19]

Worne et al.

[11] 4,349,633

[45] Sep. 14, 1982

[54] PROCESS OF MICROBIAL EXTRACTION OF HYDROCARBONS FROM OIL SANDS

[76] Inventors: Howard E. Worne, 205 Sunny Jim Dr., Medford, N.J. 08055; Irving Rabinovitch, 5762 Leger St., Cote St. Luc, Quebec H4W 2E7, Canada

[21] Appl. No.: 205,153

[22] Filed: Nov. 10, 1980

[51] Int. Cl.³ ............................................. C10G 1/00
[52] U.S. Cl. ................................................... 435/281
[58] Field of Search ......................................... 435/281

[56] References Cited

U.S. PATENT DOCUMENTS

| | | | |
|---|---|---|---|
| 2,413,273 | 12/1948 | Zobell | 195/3 |
| 2,641,566 | 6/1953 | Zobell | 195/3 |
| 3,278,335 | 10/1966 | Hitzman | 136/85 |
| 3,502,566 | 3/1970 | Raymond et al. | 208/11 |
| 3,997,398 | 12/1976 | Zajic et al. | 195/28 R |

OTHER PUBLICATIONS

Martin B. Hooking, "Physical Characterization and Microbiological Settling-Rate Modification of Aqueous Suspensions from Hot-Water-Process Oil-Sands Extraction", *Fuel,* vol. 56, Jul. 1977, pp. 334–339.

D. F. Gerson and J. E. Zajic, "Bitumen Extraction from Tar Sands with Microbial Surfactants", Canada Venezuela Oil Sands Symposium Proceedings, Canadian Institute of Minerology Special vol. 17, 1977, pp. 705–710.

David T. Gibson, "Microbial Degradation of Aromatic Compounds", *Science,* vol. 161, Sep. 13, 1968, pp. 1093–1097.

*Primary Examiner*—Robert J. Warden
*Attorney, Agent, or Firm*—Larson and Taylor

[57] ABSTRACT

A process is described for the separation of hydrocarbon residues from oil and tar sands by microbiological activity. Hydrocarbon residues are released from the sands by contacting with a suspension of oxidase-synthesizing, hydrocarbon-metabolizing microorganisms.

16 Claims, No Drawings

PROCESS OF MICROBIAL EXTRACTION OF HYDROCARBONS FROM OIL SANDS

This invention relates to a process for extraction of hydrocarbon residues from oil and tar sands by microbial activity.

Hydrocarbon residues in oil and tar sands are essentially asphaltic, bituminous and paraffinic in nature and are generally of high viscosity. The hydrocarbon residues are absorbed on a mixture of quartz sand and clay and generally the concentration of hydrocarbon residue in the sands varies from 1 to 18% by weight, depending upon the deposit. At present, hot water and high pH are commonly used for extracting oil from the sands. However, the high temperature and pH that are required for this process decompose the clay into submicron particles which then hydrate and acquire a negative charge which tends to cause the particles to form a stable gelatinous sludge which will not settle in the waste lagoons. Moreover, the waste waters themselves exhibit a high pH, and contain approximately 100,000 parts per million of residual oil.

Since the early 1940's, attempts have been made to reclaim hydrocarbons from oil deposits, tar sands, etc. by microbiological means. One process which has been described, but which has not been put into commercial operation, makes use of sulfur oxidizing bacteria to form sulfuric acid, which in turn reacts with the inorganic substrate, releasing the oil. This process is described in U.S. Pat. No. 2,413,273, issued Dec. 24, 1948 to Zobell.

Determination has also been made of the surface active substances produced by sulfur oxidizing bacteria as disclosed in the above-mentioned patent.

More recently, Zajic and his associates have conducted studies on emulsifying agents of microbiological origin, as well as on a process of microbial extraction of bitumen by the in situ formation of microbial surfactants. The results of their studies are described in, for example, U.S. Pat. No. 3,997,398, issued Dec. 14, 1976 to Zajic and Knettig, and "Bitumen Extraction from Tar Sands with Microbial Surfactants," an article by Gerson and Zajic published in the Canada Venezuela Oil Sands Symposium Proceedings, Canadian Institute of Minerology Special Volume 17, (1977) at page 705.

Investigations have now been made into the ability of various microorganisms to secrete enzyme systems which enable them to utilize hydrocarbons as a source of energy. Various microorganisms have been isolated from the soil which possess this capability. It has now been discovered that a significant number of these microorganisms have the ability to secrete various enzymes, including monooxygenase and dioxygenase enzymes, some of which are capable of oxidizing the terminal carbon of available alkane molecules forming alcohols, aldehydes and acids while others are capable of hydroxylating aromatic compounds (whether they be mononuclear such as benzene, or polynuclear such as naphthalene, anthracene or phenanthrene) forming monohydroxy, dihydroxy or polyhydroxy derivatives prior to ring fission. Surprisingly, when various actively growing oxidase-oxygenase producing microorganisms are mixed with tar and oil sands, the hydrocarbon residuese therein are released from the quartz sand and clay.

The present invention relates to a process for the separation of hydrocarbon residues from oil and tar sands which comprises contacting the sands under aerobic conditions with an aqueous medium containing hydrocarbon-metabolizing microorganisms capable of producing oxidase enzymes or oxygenase enzymes or both, in the presence of a surfactant in an amount sufficient to provide a surface tension of at most about 40 dynes/cm, whereby hydrocarbon residues are released from the sands.

Microorganisms may be used in this process either as pure cultures, or as mixed cultures being mixtures of microorganisms. The ability to secrete oxidases, for example oxidases capable of oxidizing the terminal methyl group on alkanes to alcohols, aldehydes or acids and monooxygenases or dioxygenases capable of hydroxylating aromatic compounds, varies with different microorganisms. Moreover, the composition of oil and tar sands is complex and may vary from one location to another. Thus microorganisms may be utilized in the process according to the present invention either as pure cultures, or as mixed cultures, so as to provide optimal results in achieving a separation of oil from sands obtained from any specific geographic location.

In the present investigations, a large number of microorganisms have been tested and many have been isolated which are capable of producing oxidase enzymes, including oxygenases, and of metabolizing hydrocarbons. Table 1 lists various of these microorganisms.

The selected microorganisms may be cultured in a growth medium containing Kerosene or $C_{10}$–$C_{18}$ alkane fractions as a source of assimilable carbon. Generally, most of this carbon source is consumed by the microorganisms prior to the treatment of the oil or tar sands. The growth medium also contains sufficient nutrients to provide the required quantities of nitrogen, phosphates, alkali metal salts, trace elements, etc. required for the growth of the microorganisms. The

TABLE 1

| | |
|---|---|
| *Pseudomonas* | aeruginosa |
| | arvilla |
| | alkanolytica |
| | creosotensis |
| | dacunhae |
| | desmolytica |
| | oleovorans |
| | putida |
| | rathonis |
| | salopia |
| | chloroaphis |
| | sp. |
| *Corynebacterium* | hydrocarboclastus |
| | hydrocarbooxydans |
| | petrophilum |
| | dioxydans |
| | alkanum |
| | sp. |
| *Flavobacterium* | oxydans |
| | devorans |
| | resinovorum |
| | sp. |
| *Nocardia* | butanica |
| | corallina |
| | hydrocarbonoxydans |
| | paraffinica |
| | opaca |
| | salmonicolor |
| | rubra |
| | rubropertincta |
| | amarae |
| | aurantia |
| | erythropolis |
| | minima |
| | neopaca |
| | keratolytica |
| | petroleophila |

TABLE 1-continued

| | |
|---|---|
| | saturnea |
| | sp. |
| Arthrobacter | paraffineus |
| | hydrocarboglutamicus |
| | oxydans |
| | simplex |
| | alkanicus |
| | sp. |
| Micrococcus | glutamicus |
| | paraffinolyticus |
| | auratiacus |
| | cerificans |
| | conglomeratus |
| | varians |
| | sp. |
| Mycobacterium | aurum |
| | chitae |
| | cuneatum |
| | paraffinicum |
| | phlei |
| | petroleophilum |
| | rhodochrous |
| | novum |
| | thermoresistibile |
| | terrae |
| | sp. |
| Streptomyces | argenteolus |
| | aureus |
| | californicus |
| | fradiae |
| | griseus |
| | sp. |
| Achromobacter | paraffinoclastus |
| | cycloclastes |
| | delicatulus |
| | nitriloclastes |
| | parvulus |
| | pestifer |
| | sp. |

The nutrients may be obtained from any number of sources, for example dried sewage sludge from industrial or municipal waste.

The growth medium is incubated after inoculation with a culture of microorganisms for a sufficient period to allow microorganism growth. The microorganisms may be cultured to a high concentration to form a stock solution. Alternately, the microorganisms may be cultured only until a suitable microorganism culture suspension for carrying out the process is achieved. While the concentration of microorganisms may vary, it has been found that a concentration of about $1 \times 10^9$ microorganisms/ml of medium is generally suitable for carrying out the process of the invention.

The microorganism culture suspension may be applied to oil and tar sand deposits in situ or above ground. Typically the sands are combined with the cultured microorganisms in a reaction vessel. Incubation may be continued subsequent to the combination of the microorganism culture suspension and the sands. The oil which is released from the quartz sand and clay rises to the top of the reaction vessel and may be removed by known methods.

Anionic or nonionic surfactants are typically added to the contents of the reaction vessel in order to reduce surface tension. Preferably, the surface tension of the contents of the reaction vessel is no greater than 40 dynes/cm in order to facilitate contact between oil particles and the microorganisms in the suspension. The surfactant may be incorporated in the growth medium initially, or may be added after the microorganisms have reached a specified concentration. A very small concentration of surfactant is sufficient to ensure the preferred surface tension, and is usually in the range of about 0.0001 to 0.01%. The addition of surfactants in such small concentrations is effective in reducing surface tension and facilitating the release of hydrocarbon residues from the inorganic particles in the sands. Larger concentrations may have the effect of emulsifying the released hydrocarbon residues, possibly rendering subsequent recovery more difficult. Use of non-biodegradable surfactants may result in the formation of emulsions which are difficult to break and thus a metabolizable surfactant is preferably utilized in order to facilitate release of the greatest amount of oil from the sands.

Enzymatic oxidation or oxygenation is a highly aerobic reaction. Advantageously, the process according to the present invention is carried out under conditions of aeration and/or circulation, so as to ensure that sufficient quantities of oxygen are available to ensure enzymatic activity. Circulation of the suspension of sands and microbial culture in the reaction vessel is advantageous, both in order to keep the sands in suspension, but also to produce a shearing action which facilitates oil dislodging from the sand particles as the microbiological action takes place. Circulation of the suspension also encourages the released oil to float to the surface while the heavier sand and clay particles sink to the bottom of the reaction vessel from whence they may be more easily removed.

The contents of the reaction vessel may be provided with an oxygen supply as well as maintained in a state of turbulence by discharging air jets and/or water jets into the reaction vessel containing the suspension of oil sands and microorganisms. Where the process is carried out in situ, adequate provision should be made for oxygen supply.

The process according to the present invention and particular embodiments thereof are described in the following examples. Examples 1 through 3 illustrate the recovery of oil from Athabasca oil sands utilizing mixed cultures of microorganisms. Example 4 illustrates the recovery of oil from Utah oil sands utilizing a mixed culture of microorganisms. Examples 5 through 31 illustrate oil recovery from oil sands utilizing pure cultures of microorganisms.

EXAMPLE 1

10 Liters of non-sterile medium of the following composition was charged into a 14 liter fermenter fitted with a variable speed agitator:

| | |
|---|---|
| Kerosene fraction | .3% |
| Nonylphenol ethoxylate | .001% |
| Urea | .100% |
| $K_2H\ PO_4$ | .500% |
| $KH_2\ PO_4$ | .250% |
| $Mg\ SO_4.7H_2O$ | .050% |
| $Ca\ CL_2.H_2O$ | .010% |
| $Fe\ SO_4.7H_2O$ | .010% |
| Water | Q.S. - 10 liters |
| pH 7.0 | |

The medium was inoculated with a mixed culture composed of *Bacillus subtilis, Pseudomonas fluorescens, Pseudomonas sp., Nocardia corallina,* Corynebacterim sp. and Micrococcus sp. The temperature was maintained at 25° C. along with an aeration rate of 0.5 vol./vol./min. and an agitator speed of 350 rpm. When the organism count reached $1 \times 10^9$/ml., 1,000 grams of ground Athabasca oil sands containing approximately 16% (160 grams) of bitumen was added to the fermenter. At the end of 12 hours most of the oil had separated from the sand and clay granules and was collected as a surface oil fraction. A portion of the released bitumen, because of sub-micron particle size and emulsification, remained suspended in the media. This was coalesced by using 2 ppm of a nonionic flocculating agent and separated. Oil recovery—128 gms. (80%).

The Athabasca oil sands were obtained from the Alberta Research Council Tar Sands Bank, and were accompanied by the following analysis of contents.

| | |
|---|---|
| 16.0% | bitumen |
| 1.8% | water |
| 81.7% | solids |
| 99.5% | |

0.5% discrepancy due to experimental error or loss of light ends of petroleum residues during analysis.

EXAMPLE 2

10 Liters of non-sterile medium of the following composition was charged into 14 liter fermenter fitted with a variable speed agitator:

| | |
|---|---|
| Kerosene fraction | .3% |
| Sodium alkyl aryl sulphonate | .02% |
| Urea | .100% |
| $K_2H\ PO_4$ | .500% |
| $KH_2\ PO_4$ | .250% |
| $Mg\ SO_4.7H_2O$ | .050% |
| $Ca\ CL_2.H_2O$ | .010% |
| $Fe\ SO_4.7H_2O$ | .010% |
| Water | Q.S. - 10 liters |
| pH 7.0 | |

The medium was inoculated with a mixed culture composed of Arthrobacter sp., Corynebacterium sp. and Pseudomonas sp. The temperature was maintained at 25° C. along with an aeration rate of 0.5 vol./vol./min. and an agitator speed of 400 rpm. When the organism count reached $1 \times 10^9$/ml., 1,000 grams of ground Athabasca oil sands containing approximately 7.8% (78.0 gms.) of bitumen was added to the fermenter. At the end of 12 hours most of the oil had separated from the sand and clay granules and was collected as a surface oil fraction. A portion of the released bitumen, because of sub-micron particle size and emulsification, remained suspended in the media. This was coalesced by using 2 ppm of nonionic flocculating agent and separated. Oil recovery—59.5 gms. (76.2%).

The Athabasca oil sands were obtained from the Alberta Research Council Tar Sands Bank, and were accompanied by the following analysis of contents.

| | |
|---|---|
| 7.8% | bitumen |
| 7.2% | water |
| 83.8% | solids |
| 98.8% | |

1.2% discrepancy due to experimental error or loss of light ends of petroleum residues during analysis.

EXAMPLE 3

10 liters of non-sterile medium of the following composition was charged into a 14 liter fermenter fitted with a variable speed agitator:

| | |
|---|---|
| Kerosene fraction | .3% |
| Linear alcohol ethoxylate | .01% |
| Urea | .100% |
| $K_2H\ PO_4$ | .500% |
| $KH_2\ PO_4$ | .250% |
| $Mg\ SO_4.7H_2O$ | .050% |
| $Ca\ CL_2.H_2O$ | .010% |
| $Fe\ SO_4.7H_2O$ | .010% |
| Water | Q.S. - 10 liters |
| pH 7.0 | |

The medium was inoculated with a mixed culture composed of Pseudomonas sp., Micrococcus sp. and Nocardia sp. The temperature was maintained at 25° C. along with an aeration rate of 0.5 vol./vol./min. and an agitator speed of 350 rpm. When the organism count reached $1 \times 10^9$/ml., 1,000 grams of ground Athabasca oil sand containing approximately 14.9% (149.0 grams) of bitumen was added to the fermenter. At the end of 12 hours most of the oil had separated from the sand and clay granules and was collected as a surface oil fraction. A portion of the released bitumen, because of sub-micron particle size and emulsification, remained suspended in the media. This was coalesced by using 2 ppm of a nonionic flocculating agent and separated. Oil recovery—121.6 gms. (81.6%).

The Athabasca oil sands were obtained from the Alberta Research Council Tar Sands Bank, and were accompanied by the following analysis of contents.

| | |
|---|---|
| 14.9% | bitumen |
| 2.1% | water |
| 82.4% | solids |
| 99.4% | |

0.6% discrepancy due to experimental error or loss of light ends of petroleum residues during analysis.

EXAMPLE 4

25 liters of non-sterile medium was charged into a 50 liter fermenter fitted with a Bio-Vortex ™ system of aeration and circulation. The medium was obtained from Worne Biochemicals, Inc., and had the following composition:

| | Grams/Liter |
|---|---|
| Emulsified kerosene fraction (50%) | 20.0 |
| $NH_4NO_3$ | 5.0 |
| $K_2HPO_4$ | 2.0 |
| $KH_2PO_4$ | 1.0 |
| Magnesium chelate | 1.0 |
| Calcium chelate | 0.2 |
| Iron chelate | 0.1 |
| Manganese chelate | 0.05 |
| Copper chelate | 0.01 |
| Zinc chelate | 0.1 |
| Cobalt chelate | 0.0005 |
| $Na_2MoO_4$ | 0.0005 |
| $NaVO_3.H_2O$ | 0.0001 |
| $SnCl_2.2H_2O$ | 0.0001 |
| $LiCl_3$ | 0.001 |
| NaCl | 1.00 |
| Yeast autolyzate | 2.00 |
| Marine algae extract | 1.00 |
| Water | 980.0 |
| pH 6.8–7.0 | |

The medium was inoculated with a mixed culture composed of Nocardia sp., Arthrobacter sp., Micrococcus sp., Corynebacterium sp., Pseudomonas sp. and *Bacillis subtilis*. The temperature was maintained between 22° C. and 25° C., along with an aeration rate of 1 vol.-/vol./min. and a pumping rate of 5 liters/min. When the microorganism count reached approximately $1 \times 10^9$/ml, 1 gram (0.004%) of nonylphenol ethoxylate (HLB 5-6) was added to the fermenter to reduce the surface tension to less than 40 dynes/cm. This was followed by 3,000 grams of ground Utah oil sands containing 12.8% (384 grams) of hydrocarbon. At the end of 12 hours most of the oil had separated from the sand and clay particles. The pumping was stopped but the aeration was continued for an additional 30 minutes to help bring the oil to the surface. The aeration was stopped and the surface oil was collected and dried over anhydrous $CaSO_4$. A portion of the released hydrocarbon, because of particle size and emulsification, remained suspended in the medium. This was coalesced and removed from the spent medium by treatment with 5 ppm (62 mg.) of sodium aluminate. Total oil recovery was 355 gm. (92.4%).

| | |
|---|---|
| Surface oil recovery | 332.0 gm. |
| Medium oil recovery | 23.0 gm. |
| Total released oil | 335.0 gm. |
| Residual oil in sand | 12.8 gm. |
| Hydrocarbon loss | 16.2 gm. |
| Total hydrocarbons | 384.0 gm. |

EXAMPLES 5 to 31

To determine the efficiency of axenic microbial cultures in oil recovery from oil and tar sands, 500 ml Erlenmeyer flasks, fitted with a ¾ inch SS #304 baffle, were charged with 75 ml of medium obtained from Worne Biochemicals, Inc. and inoculated with the desired microorganisms. The composition of the medium has been described in Example 4. The microorganisms tested were obtained from Worne Biochemicals, Inc.

The flasks were placed in a rotary shaking incubator operating at 175 cycles per minute with an amplitude of 1.5 centimeters to achieve an aeration rate equivalent to 2 ppm of dissolved oxygen. The temperature was maintained between 22° C. and 25° C. and when the cell count reached $1 \times 10^9$/ml, 0.001% nonylphenol ethoxylate (HLB 5-6) was added to the flasks to reduce the surface tension to less than 40 dynes/cm., followed by 10 gms. of Athabasca oil sands containing approximately 16% hydrocarbon. The rotary shaking rate was raised to 200 cycles/min. to increase the level of dissolved oxygen and the biological reaction was allowed to continue for 8-12 hours. Upon completion of the incubation period the flasks were removed from the rotary shaker and allowed to settle.

The surface layer of oil which had separated from the sand was then filtered by vacuum through a Buchner funnel fitted with a fiberglass disc. The retained solids in the funnel were extracted with benzene (B.P. 80°-81° C.) to remove the remaining oil, followed by flash vacuum evaporation to remove the benzene and obtain the residual oil. The extracted solids were dried in an oven at 110° C. for 12 hours prior to weighing. The filtrate was extracted in a modified Hershberg-Wolfe liquid-liquid extractor with benzene (B.P. 80°-81° C.) to recover the emulsified oil. The benzene layer was separated, dried and then evaporated in a Buchler rotary flash evaporator under vacuum to recover the oil residue. Each of the individual fractions were weighed to determine the efficiency of microbiological oil recovery from the oil sands and, in addition, the hydrocarbon losses from the processing were determined. The results are set out in Table II, wherein the W.B.I. No. refers to the culture collection identification number assigned by Worne Biochemicals, Inc.

TABLE III

EFFICIENCY OF HYDROCARBON RELEASE FROM OIL AND TAR SANDS BY 27 CULTURES OF AXENIC MICROORGANISMS

| Microorganism (W.B.I. No.) | Wt. of Oil Surface Layer | Wt. of Oil Extracted From Sand Residue | Wt. Oil Extracted From Spent Media | Total Wt. of Oil Recovered | % Hydrocarbon Loss |
|---|---|---|---|---|---|
| *Pseudomonas arvilla* (1GA13-2) | 0.864 gm. (54.0%) | 0.200 gm. (12.5%) | 0.357 gm. (22.3%) | 1.421 gm. | 11.2 |
| *Pseudomonas dacunhae* (1GA19-1) | 0.918 gm. (57.4%) | 0.235 gm. (14.7%) | 0.264 gm. (16.5%) | 1.417 gm. | 11.4 |
| *Pseudomonas desmolytica* (1GA36-1) | 0.808 gm. (50.5%) | 0.192 gm. (12.0%) | 0.348 gm. (21.7%) | 1.348 gm. | 15.8 |
| Pseudomonas sp. (1GA0-90) | 1.005 gm. (62.8%) | 0.103 gm. (6.4%) | 0.248 gm. (15.5%) | 1.356 gm. | 15.3 |
| Pseudomonas sp. (1GA0-100) | 0.979 gm. (61.2%) | 0.114 gm. (7.1%) | 0.293 gm. (18.3%) | 1.386 gm. | 13.4 |
| *Arthrobacter oxydans* (4LF4-1) | 0.885 gm. (55.3%) | 0.333 gm. (20.8%) | 0.165 gm. (10.3%) | 1.383 gm. | 13.6 |
| *Arthrobacter simplex* (4LF3-1) | 0.984 gm. (61.5%) | 0.179 gm. (11.2%) | 0.186 gm. (11.6%) | 1.349 gm. | 15.7 |
| Arthrobacter sp. (4LF20-1) | 0.955 gm. (59.7%) | 0.200 gm. (12.5%) | 0.206 gm. (12.9%) | 1.361 gm. | 15.4 |
| *Corynebacterium hydrocarbooxydans* (4LA12-1) | 0.960 gm. (60.0%) | 0.189 gm. (11.8%) | 0.234 gm. (14.6%) | 1.383 gm. | 13.6 |
| *Corynebacterium dioxydans* (4LA11-1) | 0.942 gm. (58.9%) | 0.195 gm. (12.2%) | 0.296 gm. (18.5%) | 1.433 gm. | 10.4 |
| Corynebacterium sp. (4LA20-1) | 0.858 gm. (53.6%) | 0.299 gm. (18.7%) | 0.300 gm. (18.7%) | 1.457 gm. | 9.0 |
| *Flavobacterium oxydans* (4CC21-1) | 0.787 gm. (49.2%) | 0.405 gm. (25.3%) | 0.248 gm. (15.5%) | 1.440 gm. | 10.0 |
| *Flavobacterium devorans* (4CC12-1) | 0.728 gm. (45.5%) | 0.418 gm. (26.1%) | 0.311 gm. (19.4%) | 1.457 gm. | 9.0 |
| Flavobacterium sp. (4CC25-1) | 0.758 gm. (47.4%) | 0.378 gm. (23.6%) | 0.292 gm. (18.2%) | 1.428 gm. | 10.8 |

TABLE III-continued

EFFICIENCY OF HYDROCARBON RELEASE FROM OIL AND TAR SANDS BY 27 CULTURES OF AXENIC MICROORGANISMS

| Microorganism (W.B.I. No.) | Wt. of Oil Surface Layer | Wt. of Oil Extracted From Sand Residue | Wt. Oil Extracted From Spent Media | Total Wt. of Oil Recovered | % Hydrocarbon Loss |
|---|---|---|---|---|---|
| Nocardia corallina (5BA13-1) | 0.947 gm. (59.2%) | 0.208 gm. (13.0%) | 0.320 gm. (20.0%) | 1.475 gm. | 7.8 |
| Nocardia rubra (5BA17-2) | 1.005 gm. (62.8%) | 0.175 gm. (10.9%) | 0.303 gm. (18.9%) | 1.483 gm. | 7.4 |
| Nocardia opaca (5BA4-2) | 0.939 gm. (58.7%) | 0.200 gm. (12.5%) | 0.263 gm. (16.4%) | 1.402 gm. | 12.4 |
| Nocardia salmonicolor (5BA15-1) | 0.902 gm. (56.4%) | 0.210 gm. (13.1%) | 0.324 gm. (20.2%) | 1.436 gm. | 10.3 |
| Nocardia hydrocarbonoxydans (5BA36-2) | 0.979 gm. (61.2%) | 0.181 gm. (11.3%) | 0.267 gm. (16.7%) | 1.427 gm. | 10.8 |
| Nocardia sp. (5BA34-1) | 0.975 gm. (60.9%) | 0.183 gm. (11.4%) | 0.293 gm. (18.3%) | 1.451 gm. | 9.6 |
| Micrococcus paraffinolyticus (4GA25-1) | 0.832 gm. (52.0%) | 0.282 gm. (17.6%) | 0.248 gm. (15.5%) | 1.362 gm. | 14.9 |
| Micrococcus sp. (4GA31-1) | 0.838 gm. (52.4%) | 0.272 gm. (17.0%) | 0.266 gm. (16.6%) | 1.376 gm. | 14.0 |
| Mycobacterium rhodochrous (5AA37-1) | 0.632 gm. (39.5%) | 0.504 gm. (31.5%) | 0.322 gm. (20.1%) | 1.458 gm. | 8.9 |
| Mycobacterium sp. (5AA38-2) | 0.773 gm. (48.3%) | 0.363 gm. (22.7%) | 0.284 gm. (17.7%) | 1.420 gm. | 11.3 |
| Achromobacter cycloclastes (4CB8-1) | 0.682 gm. (42.6%) | 0.397 gm. (24.8%) | 0.298 gm. (18.6%) | 1.377 gm. | 14.0 |
| Achrombacter pestifier (4CB9-1) | 0.720 gm. (45.9%) | 0.405 gm. (25.3%) | 0.325 gm. (20.3%) | 1.450 gm. | 9.4 |
| Achrombacter sp. | 0.826 gm. | 0.423 gm. (26.4%) | 0.269 gm. (16.8%) | 1.518 gm. | 5.2 |

The embodiments of the invention in which an exclusive property or privilege is claimed are defined as follows:

1. A process for the separation of hydrocarbon residues from oil and tar sands which comprises contacting the sands under aerobic conditions with an aqueous medium containing hydrocarbon-metabolizing microorganisms capable of producing oxidase enzymes or oxygenase enzymes or both, in the presence of an added surfactant in an amount sufficient to provide surface tension of at most about 40 dynes/cm and in the presence of oxygen in an amount sufficient to ensure activity of said enzymes, whereby hydrocarbon residues are released from the sands.

2. The process according to claim 1, wherein terminal carbons of alkane molecules in the hydrocarbon residues are oxidized or aromatic compounds in the hydrocarbon residues are hydroxylated or both, whereby the hydrocarbon residues are released from the sands.

3. The process according to claim 1 or 2, wherein the sands are maintained in suspension in the medium by turbulence.

4. The process according to claim 1, when carried out in a reaction vessel.

5. The process according to claim 1, wherein molecular oxygen or air is introduced during the process.

6. A process for the extraction of hydrocarbon residues from oil and tar sands which comprises:
culturing hydrocarbon-metabolizing microorganisms capable of producing oxidase enzymes or oxygenase enzymes or both, in an aqueous medium,
contacting oil or tar sands with the microorganism-containing medium in the presence of an added surfactant in an amount sufficient to provide a surface tension of at most about 40 dynes/cm, agitating the mixture of sands and microorganism-containing medium under aerobic conditions to provide oxygen in an amount sufficient to ensure activity of said enzymes, whereby the hydrocarbon residues are released from the sands,
and recovering the hydrocarbon residues.

7. The process according to claim 1, 2 or 6, wherein the concentration of microorganisms in the medium is about $1 \times 10^9$ microorganism/ml.

8. The process according to claim 1, 2 or 6, wherein the surfactant is anionic or nonionic and is biodegradable.

9. The process according to claim 1, 2 or 6, wherein the concentration of surfactant with respect to medium is in the range of about 0.01 to 0.0001%.

10. The process according to claim 1, 2 or 6, wherein the microorganisms comprise a mixed culture selected from the group consisting of microorganisms of the species Pseudomonas, Corynebacterium, Flavobacterium, Nocardia, Arthrobacter, Micrococcus, Mycobacterium, Streptomyces, Achromobacter and Bacillus.

11. The process according to claim 1, 2 or 6, wherein the microorganisms comprise a mixed culture of Bacillus subtilis, Pseudomonas fluorescens, Pseudomonas sp., Nocardia corallina, Corynebacterium sp. and Micrococcus sp.

12. The process according to claim 1, 2 or 6, wherein the microorganisms comprise a mixed culture of Arthrobacter sp., Corynebacterium sp. and Pseudomonas sp.

13. The process according to claim 1, 2 or 6, wherein the microorganisms comprise a mixed culture of Pseudomonas sp., Micrococcus sp. and Nocardia sp.

14. The process according to claim 1, 2 or 6, wherein the microorganisms comprise a mixed culture of Nocardia sp., Arthrobacter sp., Micrococcus sp., Corynebacterim sp., Pseudomonas sp. and Bacillis subtilis.

15. The process according to claim 1, 2 or 6, wherein the microorganisms comprise a pure culture selected from the group consisting of microorganisms of the species Pseudomonas, Corynebacterium, Flavobacterium, Nocardia, Arthrobacter, Micrococcus, Mycobacterium, Streptomcyes, Achrombacter, and Bacillus.

16. The process according to claim 1, 2 or 6, wherein the microorganisms comprise a pure culture selected from the group consisting of *Pseudomonas arvilla, Pseudomonas dacunhae, Pseudomonas desmolytica,* Pseudomonas sp. *Arthrobacter oxydans, Arthrobacter simplex,* Arthrobacter sp., *Corynebacterium hydroxycarbooxydans, Corynebacterium dioxydans,* Corynebacterium sp., *Flavobacterium oxydans, Flavobacterium devorans,* Flavobacterium sp., *Nocardia corallina, Nocardia rubra, Nocardia opaca, Nocardia salmonicolor, Nocardia hydrocarbonoxydans,* Nocardia sp., *Micrococcus paraffinolyticus,* Micrococcus sp., *Mycobacterim rhodochrous,* Mycobacterium sp., *Achromobacter cycloclastes, Achromobacter pestifer* and Achromobacter sp.

* * * * *